(12) United States Patent
McMichael

(10) Patent No.: US 10,493,000 B2
(45) Date of Patent: Dec. 3, 2019

(54) ENTERAL FEEDING SATIATION DEVICE

(71) Applicant: Avent, Inc., Alpharetta, GA (US)

(72) Inventor: Donald McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 15/543,120

(22) PCT Filed: Aug. 17, 2016

(86) PCT No.: PCT/US2016/047286
§ 371 (c)(1),
(2) Date: Jul. 12, 2017

(87) PCT Pub. No.: WO2018/034658
PCT Pub. Date: Feb. 22, 2018

(65) Prior Publication Data
US 2019/0159972 A1 May 30, 2019

(51) Int. Cl.
*A61J 15/00* (2006.01)
*A61F 5/00* (2006.01)

(52) U.S. Cl.
CPC ......... *A61J 15/0046* (2013.01); *A61F 5/0036* (2013.01); *A61J 15/0015* (2013.01);
(Continued)

(58) Field of Classification Search
CPC ................ A61J 15/0046; A61J 15/0092; A61J 15/0049; A61J 15/0015; A61J 15/0036;
(Continued)

(56) References Cited

U.S. PATENT DOCUMENTS

| 6,019,746 A | 2/2000 | Picha et al. |
|---|---|---|
| 6,675,809 B2 | 1/2004 | Stack et al. |

(Continued)

FOREIGN PATENT DOCUMENTS

| FR | 2 983 399 A1 | 6/2013 |
|---|---|---|
| RU | 2 455 033 C2 | 7/2012 |

(Continued)

OTHER PUBLICATIONS

International Search Report and Written Opinion, dated May 12, 2017, 12 pages.

*Primary Examiner* — Bradley J Osinski
*Assistant Examiner* — Hamza A Darb
(74) *Attorney, Agent, or Firm* — Dority & Manning, P.A.

(57) ABSTRACT

Devices for inducing satiety in enterally fed patients are provided. In one aspect, an enteral feeding device is provided that includes a catheter tube and an expandable bladder secured to a distal end of the catheter tube. The expandable bladder is positionable within a body lumen of a patient for receiving and dispensing nutrients to the patient. In another aspect, a satiety-inducing device for continuously dispensing nutrients to a patient is provided that includes an enteral feeding tube and an expandable bladder secured to the feeding tube near a distal end of the feeding tube such that the expandable bladder is positionable within a body lumen of the patient. The expandable bladder expands upon receipt of nutrients to occupy a volume of the body lumen and contracts as nutrients are continuously dispensed to the patient.

20 Claims, 4 Drawing Sheets

(52) U.S. Cl.
CPC ....... *A61J 15/0042* (2013.01); *A61J 15/0049* (2013.01); *A61J 15/0057* (2013.01); *A61J 15/0092* (2013.01)

(58) Field of Classification Search
CPC ................ A61J 15/0057; A61J 15/0038; A61J 15/0069; A61F 5/0036; A61F 5/0003; A61F 5/0069; A61F 5/003; A61M 2025/0233; A61M 2025/105
See application file for complete search history.

(56) References Cited

U.S. PATENT DOCUMENTS

| | | |
|---|---|---|
| 7,146,984 B2 | 12/2006 | Stack et al. |
| 7,967,780 B2 | 6/2011 | Goebel |
| 8,628,554 B2 | 1/2014 | Sharma |
| 8,876,761 B2 | 11/2014 | Albrecht et al. |
| 9,295,573 B2 | 3/2016 | Snow et al. |
| 2005/0159769 A1 | 7/2005 | Alverdy |
| 2009/0182264 A1 | 7/2009 | Eike |
| 2010/0106130 A1 | 4/2010 | Solovay et al. |
| 2011/0118650 A1 | 5/2011 | Nihalani |
| 2011/0184229 A1* | 7/2011 | Raven .................. A61F 5/0056 600/37 |
| 2013/0211190 A1 | 8/2013 | Fishler et al. |
| 2013/0268089 A1 | 10/2013 | Weiss et al. |
| 2014/0303746 A1 | 10/2014 | Forsell |
| 2016/0030219 A1 | 2/2016 | Babkes et al. |

FOREIGN PATENT DOCUMENTS

| | | |
|---|---|---|
| WO | WO 2007/087254 A2 | 8/2007 |
| WO | WO 2014/153267 A2 | 9/2014 |

* cited by examiner

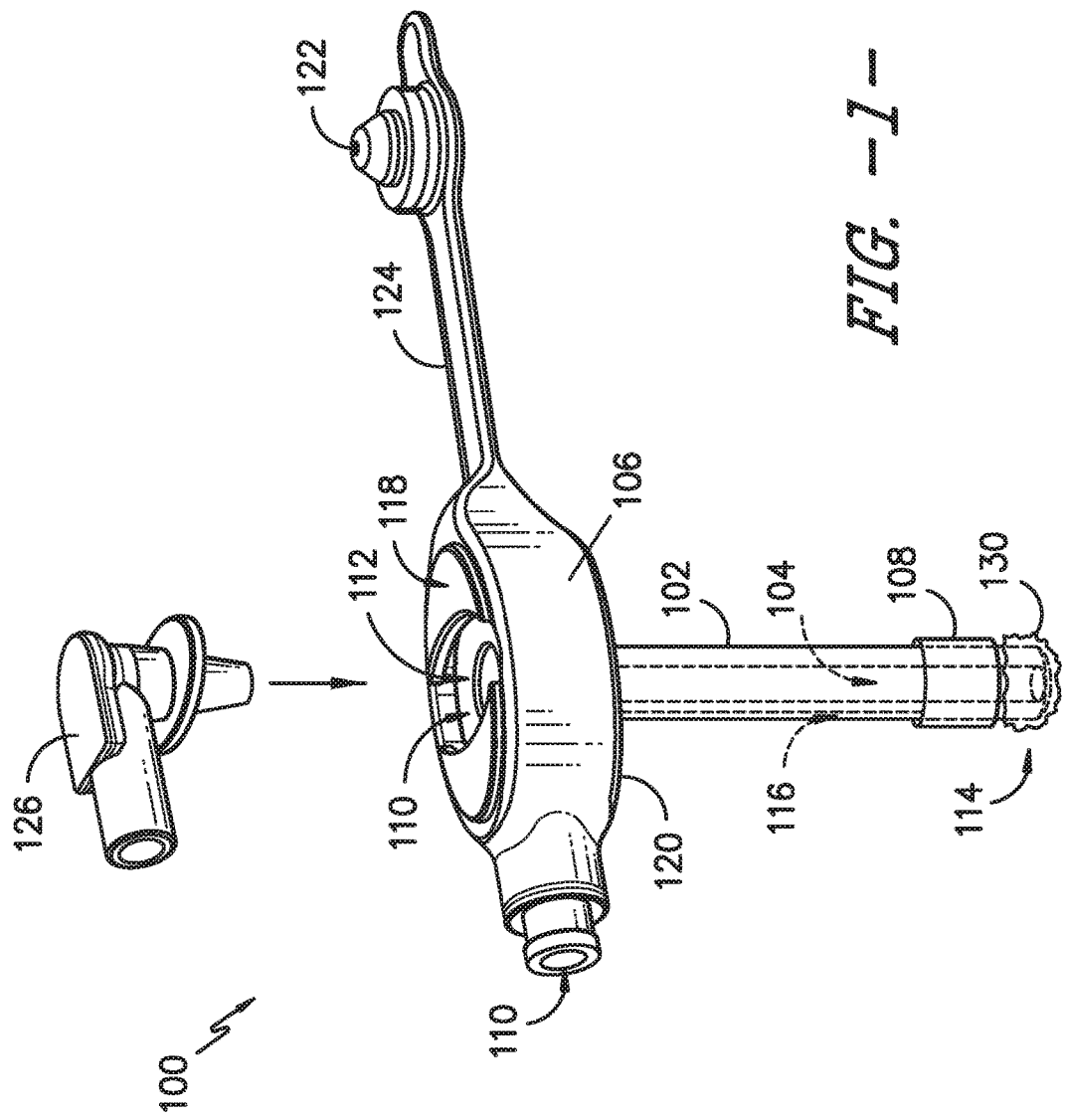
FIG. -1-

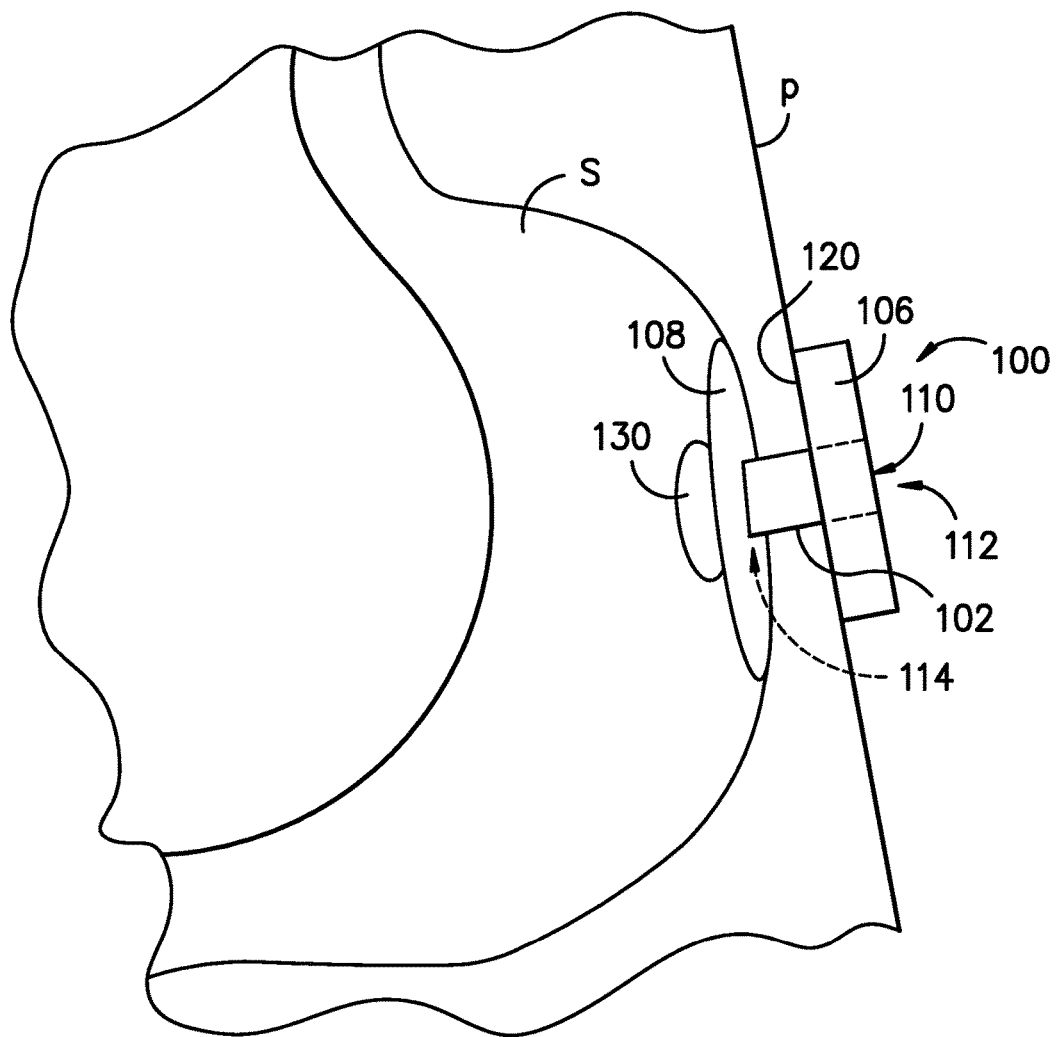
FIG. -2A-

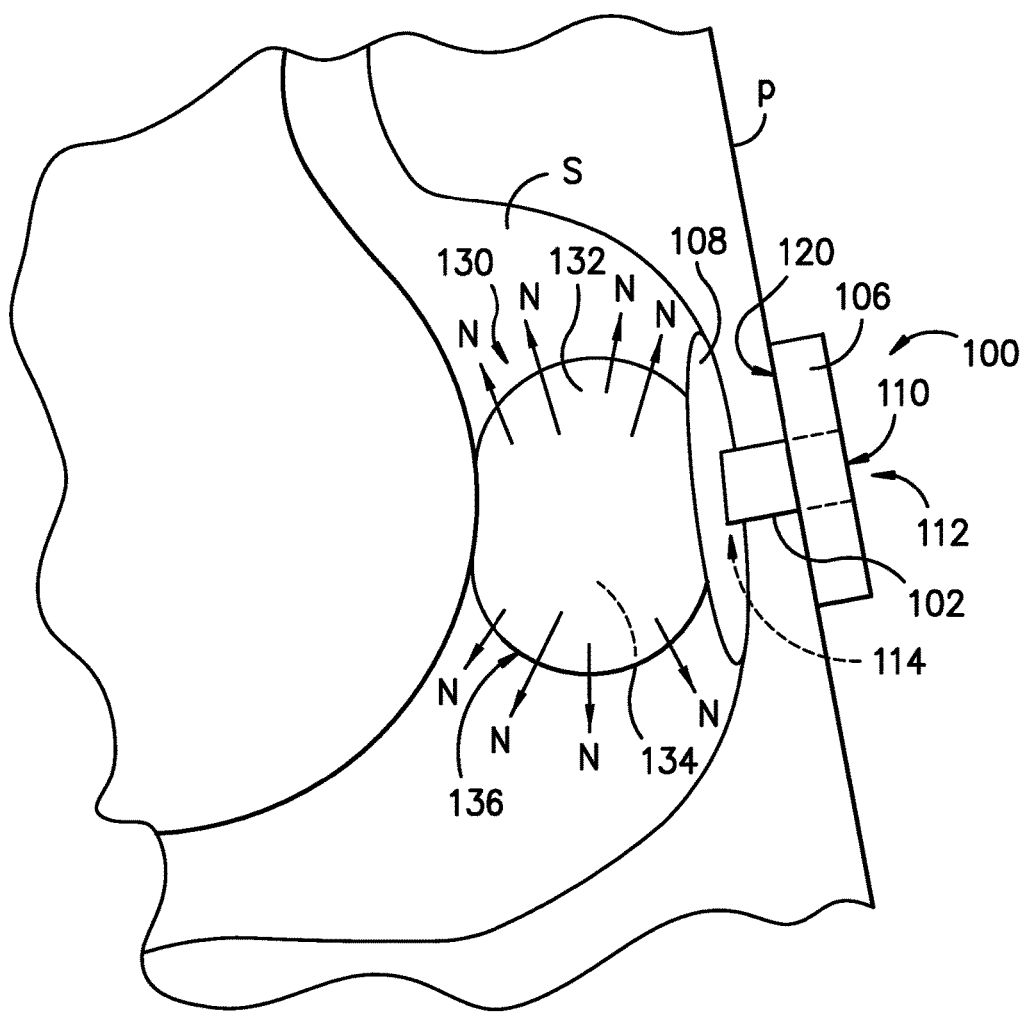
FIG. -2B-

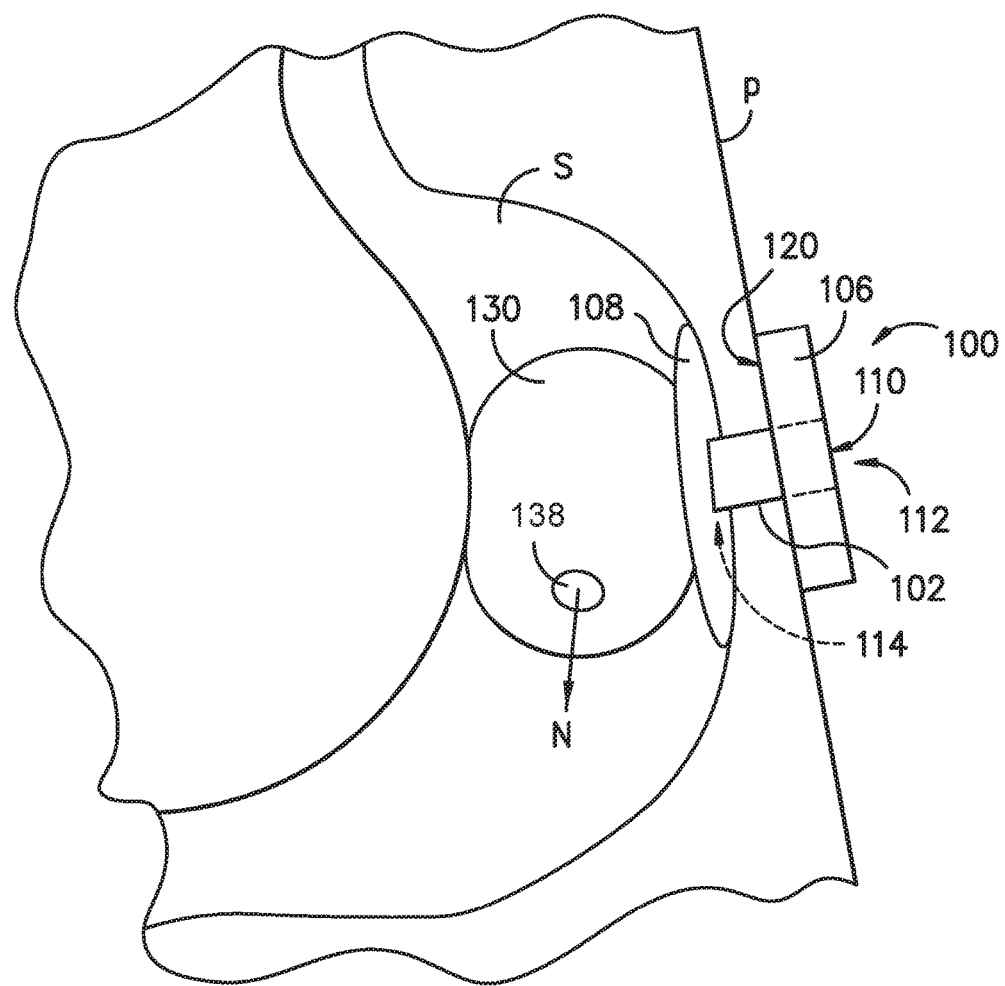
FIG. -2C-

ENTERAL FEEDING SATIATION DEVICE

CROSS-REFERENCE TO RELATED APPLICATIONS

This application is a national phase of and claims priority to PCT/US2016/47286, filed Aug. 17, 2016, the contents of which are incorporated herein by reference thereto.

FIELD OF THE INVENTION

The present invention relates to devices for enteral feeding of a patient. More particularly, the present invention relates to devices for inducing satiation of enterally fed patients.

BACKGROUND

Numerous situations exist in which interior parts of the human body needs to be catheterized through an artificial stoma to achieve a desired medical goal. Relatively common situations are for drainage of retained fluids and administering nutritional solutions or medicines directly into the stomach or intestines. For these situations a stoma is formed percutaneously and an indwelling device is placed through the stoma. By way of example the surgical opening and/or the procedure to create a stoma spanning between the stomach or intestinal wall and the exterior of the skin is commonly referred to as "gastrostomy." A device with a catheter component, e.g., a feeding tube, placed through such a stoma allows injection of feeding solutions through the tube to provide nutrients directly to the stomach or intestines (known as enteral feeding). A variety of different devices intended for enteral feeding have been developed over the years, including some having a "low profile" relative to that portion which sits on a patient's skin, as well as those having the more traditional or non-low profile configuration. These percutaneous transconduit devices (sometimes referred to as "percutaneous transconduit catheters") are frequently referred to as "gastrostomy tubes," "percutaneous gastrostomy tubes," "PEG tubes," or "enteral feeding tubes." U.S. Pat. No. 6,019,746 for a "Low Profile Balloon Feeding Device" issued to Picha et al. on Feb. 1, 2000, provides an example of one device.

As indicated above, there are a variety of instances in which it may be necessary to use a catheter, one of which is the not uncommon reaction following major surgery in which a patient's stomach function is impaired for a period of time. In addition to the need to supply or supplement the body with a certain level of nutrients and the like following surgery as well as in other instances of impaired or limited gastric functionality, a further issue is that an unfed gut can become a source of bacteria that gets into the bloodstream. These types of problems may be resolved by the introduction of nutrients through an enteral feeding device tube properly inserted through the patient's abdominal wall, gastric wall, pylorus, duodenum, and/or into the jejunum beyond the Ligament of Treitz.

Typically, patients who are enterally fed and who have reflux or aspiration issues are denied the feeling of being satiated or "full" because such patients are fed jejunally, i.e., the nutrients are provided directly into the small intestine, or are fed on a continuous drip feed into the stomach, e.g., for 12 hours or longer. Thus, such patients usually are not fed on a "normal" or typical feeding regimen, e.g., two or three times a day, and may be denied the feeling of having eaten enough, which feeling generally occurs when the stomach swells to accept a bolus of food.

Accordingly, an enteral feeding device that provides improved satiation for a patient would be useful. More particularly, an enteral feeding device that simulates or replicates a satiated feeling while also providing continuous feeding would be beneficial. Further, an enteral feeding device incorporating a balloon for internal positioning within a patient that accepts a bolus of food and provides continuous feeding to the patient would be advantageous.

SUMMARY

Aspects and advantages of the invention will be set forth in part in the following description, or may be obvious from the description, or may be learned through practice of the invention.

In one aspect, the present subject matter is directed to an enteral feeding device. The device includes a catheter tube having a distal end and a proximal end; a first retainer secured to the catheter tube at the proximal end of the catheter tube; and a second retainer secured to the catheter tube at the distal end of the catheter tube. The first retainer is an external retainer for deployment outside a patient's body, and the second retainer is an indwelling retainer for deployment within a body lumen of the patient. The device also includes an expandable bladder secured to the catheter tube at the distal end of the catheter tube. The expandable bladder is positionable within the body lumen of the patient for receiving and dispensing nutrients to the patient.

In some embodiments, the bladder is a permeable membrane. In other embodiments, the device comprises a flow control valve for dispensing nutrients from the bladder. The bladder may be constructed from an elastic material or any other material, e.g., that is suitable for repeated expansion and contraction.

In various embodiments, the body lumen is the patient's stomach such that the bladder is positionable within the patient's stomach. The bladder may expand to receive a bolus dose of nutrients, and more particularly, the bladder may expand to occupy a volume of the body lumen of the patient. In an exemplary embodiment, the nutrients are dispensed at a continuous rate, but in other embodiments, the nutrients may be dispensed at other appropriate rates or intervals.

In yet other embodiments, the first retainer is a base of a low profile enteral feeding device, and in still other embodiments, the second retainer is an inflatable balloon. Other configurations of the device may be used as well.

In another aspect, the present subject matter is directed to a satiety-inducing device for continuously dispensing nutrients to a patient. The device comprises an enteral feeding tube having a distal end and a proximal end. The distal end is positionable within a body lumen of the patient. A retainer is secured to the feeding tube at the proximal end of the feeding tube. The retainer is an external retainer for deployment outside the patient's body. The device further includes an expandable bladder secured to the feeding tube near the distal end of the feeding tube such that the expandable bladder is positionable within the body lumen of the patient. The expandable bladder expands upon receipt of nutrients to occupy a volume of the body lumen and contracts as nutrients are continuously dispensed to the patient.

In some embodiments of the satiety-inducing device, the bladder is a permeable membrane, and in other embodiments, the device includes a flow control valve for controlling a flow rate of nutrients from the bladder. In an exemplary embodiment, the bladder is constructed from an elastic material, but in other embodiments, the bladder may be made from any other material, e.g., that is suitable for repeated expansion and contraction. Further, in some embodiments, the body lumen is the patient's stomach such that the bladder is positionable within the patient's stomach.

Additionally or alternatively, the retainer may be a base of a low profile enteral feeding device. In some embodiments, the retainer is a first retainer and the device further comprises a second, indwelling retainer. For example, the second retainer may be an inflatable balloon, but other types or configurations of indwelling retainers also may be used. Moreover, other configurations of the satiety-inducing device may be used as well.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 is a schematic cross-section view of an enteral feeding or satiety-inducing device according to an exemplary embodiment of the present subject matter.

FIG. 2A is a schematic view of the enteral feeding or satiety-inducing device of FIG. 1 positioned within a body lumen of a patient and with an expandable bladder in a deflated or unexpanded state, according to an exemplary embodiment of the present subject matter.

FIG. 2B is a schematic view of the enteral feeding or satiety-inducing device of FIG. 2A with the expandable bladder in an inflated or expanded state, according to an exemplary embodiment of the present subject matter.

FIG. 2C is a schematic view of the enteral feeding or satiety-inducing device of FIG. 2A with the expandable bladder in an inflated or expanded state, according to another exemplary embodiment of the present subject matter.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

The present invention relates to a non-vascular catheter device, e.g., an enteral feeding device or the like, having a catheter tube, an external retainer (e.g., base deployed outside the human body), and an indwelling retainer that is deployed within a lumen or cavity of a patient's body (i.e., a non-vascular lumen or cavity of the body such as, for example, a gastric lumen, jejunum, peritoneal cavity or the like). For example, the indwelling retainer is a retention mechanism of the catheter device that prevents the catheter device from being pulled out of the patient, and the indwelling retainer may be inserted into the body lumen through a stoma. The insertion through the stoma may be from outside the body or it may be performed from inside the body using endoscopic techniques. In this context, the term "insertion" should be understood as putting in or introducing the catheter tube in place in a stoma so that the base is deployed outside the human body and the indwelling retainer is deployed within a non-vascular lumen or cavity. Generally speaking, the catheter device is an enteral feeding device such as, for example, a configurable PEG or "C-PEG" device.

Referring now to FIG. 1 of the drawings, a side view schematic illustration is provided of a non-vascular catheter device according to an exemplary embodiment of the present subject matter. More particularly, the non-vascular catheter device of the exemplary embodiment of FIG. 1 is an enteral feeding device 100 (which may also be referred to as a "PEG" device) including a flexible catheter 102 (which may also be referred to as a "tube," "feeding tube," or "shaft") having walls defining at least one lumen 104 therethrough. The enteral feeding device 100 further includes a base 106 deployed outside a body of a patient P (FIGS. 2A-2C) and an indwelling retainer 108, which is deployed within a non-vascular body lumen of the patient P (e.g., a gastric lumen such as the patient's stomach). The base 106 also may be a first or external retainer of the enteral feeding device 100, while the indwelling retainer 108 is a second, internal retainer of device 100.

Generally speaking, base 106 of the enteral feeding device 100 has one or more openings or ports 110 allowing access, e.g., to the lumen(s) 104 of catheter 102. As shown in FIG. 1, the flexible catheter 102 has a proximal end 112, a distal end 114, a longitudinal axis A, a width W, and a length L. Moreover, in the depicted embodiment of FIG. 1, catheter 102 is positioned through the base 106 in communication with the one or more ports 110 in the base. The walls of the catheter 102 define the one or more lumens 104, which extend from the port(s) 110 in the base 106 to the distal end 114 of the catheter 102. The lumen(s) 104 may be in communication with an opening or openings in the second retainer 108.

The second retainer 108 may be a conventional molded flexible retainer or it may be a configurable retainer that changes from an "insertion" or "removal" state, in which the retainer has a diameter that is generally about the same as the catheter portion of the enteral feeding device, to an expanded "retention" or "deployed" state, in which the retainer takes on an expanded shape that has a substantially larger diameter than the catheter portion of the device. Such configurable PEG devices may be referred to as C-PEG devices. In various embodiments, a configurable second retainer 108 may be an inflatable or a non-inflatable retainer, and the expanded shape may be a mushroom, dome, spherical, hemispherical, doughnut, or other suitable shape.

The second retainer 108 is secured away from the proximal end 112 of the catheter 102 of the enteral feeding device 100. More particularly, the second retainer 108 is secured to catheter 102 near the distal end 114 of catheter 102. As noted above, the second retainer 108 is an indwelling retainer configured to be deployed within a non-vascular body lumen, such as, e.g., a patient's stomach. In an exemplary embodiment, the second retainer 108 is an inflatable balloon 108 that receives fluid via an inflation lumen 116, which may extend through the base 106. In other embodiments, the second retainer 108 may be a non-inflatable retainer such that inflation lumen 116 is unnecessary.

The base 106, which, as previously stated, may be a first, external retainer configured to be deployed outside the patient's body, also may be secured on the catheter 102. As shown in FIG. 1, the first retainer 106 is secured to catheter 102 proximal to the second retainer 108, more specifically, at or near the proximal end 112 of catheter 102. In the exemplary embodiment of FIG. 1, the first retainer or base 106 is the base of a low profile PEG device and has a proximal surface 118 and a distal surface 120. When the enteral feeding device 100 is positioned for operation, i.e., for providing nutrients to a body lumen of the patient P, the distal surface 120 is positioned against or adjacent the patient's skin. As previously described, the base 106 may define one or more ports 110. For example, the base 106 may define one port 110 to provide access to catheter 102 and a second port 110 to provide access to inflation lumen 116 for inflating balloon 108. A plug 122 may be included for each port 110 such that, e.g., the ports may be closed when not in use. One or more of the plugs 122 may be attached to the base 106 by a tether 124. Of course, in other embodiments, each plug 122 may be separate from, or not attached to, the base 106. Additionally or alternatively, one or more of the ports 110 may incorporate a one-way valve that allows an ingress of fluid, e.g., nutrients for delivery to the patient P, through the port 110 but prevents an egress of fluid through the port 110.

Referring still to FIG. 1, in some embodiments, a connector 126 may be used to connect the catheter or feeding tube 102 with a source of a nutrient solution, such as a syringe or other appropriate injector, to be provided to the patient P. The connector 126 may be positioned on the base 106 such that the connector 126 and, thereby, the nutrient source are in fluid communication with the lumen 104 of the catheter 102 so that nutrients may be delivered to the patient P. It will be appreciated that the connector 126 may have any suitable configuration for connecting the nutrient source with the enteral feeding device 100 or that, in appropriate embodiments, the connector 126 may be omitted.

As further illustrated in FIG. 1, the enteral feeding device 100 includes an expandable bladder 130 secured to the catheter tube 102 at or near the distal end 114 of the catheter tube. As described in greater detail below, the bladder 130 expands upon receipt of a bolus of nutrients or food, thereby occupying a volume of a body lumen such as a patient's stomach and inducing a feeling of satiety in the patient. The bladder 130 is configured to dispense the food or nutrients at a continuous rate to maintain the clinical benefits of continuous feeding. Accordingly, the enteral feeding device 100 comprising bladder 130 also may be described as a satiety-inducing device 100 for continuously dispensing nutrients to a patient.

Similar to second retainer 108, the bladder 130 is an indwelling component of the enteral feeding device 100, i.e., bladder 130 is positionable within a body lumen of the patient P, such as the patient's stomach S as shown in FIGS. 2A through 2C. Referring particularly to FIG. 2A, a schematic depiction is provided of an exemplary enteral feeding device 100 in place for use with a patient P. As shown in the depicted exemplary embodiment, the catheter or feeding tube 102 is positioned through a stoma formed from a wall of the stomach S through the patient's skin such that the catheter 102 spans from an interior of the stomach S to an exterior of the patient P. The distal surface 120 of the base 106 is positioned in contact with the patient's skin, and the second, indwelling retainer 108 is deployed within the patient's stomach S to retain the enteral feeding device in a desired position for enteral feeding.

As further depicted in FIG. 2A, the bladder 130 is in a generally deflated or unexpanded state. However, as the bladder 130 receives nutrients to dispense to patient P, the bladder 130 expands as shown in FIGS. 2B and 2C. Referring particularly to the schematic depiction of FIG. 2B, the bladder 130 may receive a bolus dose of nutrients or a bolus of food and expand to occupy a volume of the patient's stomach S. As such, upon receipt of the nutrients, the bladder 130 is in an inflated or expanded state. In the exemplary embodiment of FIG. 2B, the expandable bladder 130 is a permeable membrane 132 that allows the nutrients N to slowly permeate through the membrane and into the patient's stomach S. More particularly, the permeable membrane may allow the nutrients N to pass from an interior 134 of the bladder 130 to beyond an outer surface 136 of the bladder. In various embodiments, the permeable membrane may be made from Gortex® or another suitable permeable material. The material forming permeable membrane may be selected such that the nutrients N permeate the material at a substantially constant or continuous rate, e.g., that approximates continuous drip feeding of known enteral feeding assemblies.

Referring now to the schematic depiction of FIG. 2C, in another exemplary embodiment, the bladder 130 may comprise a flow control valve 138 that controls a flow rate at which the nutrients are dispensed from bladder 130 to the patient P. In some embodiments, the flow control valve 138 may be a pressure compensated flow control valve mounted on or incorporated into the bladder 130. Other suitable valves may be used as well, and in some embodiments, bladder 130 may comprise more than one flow control valve 138.

It will be appreciated that, in some embodiments, the bladder 130 may be a permeable membrane that comprises a flow control valve 138. Further, whether the bladder 130 is a permeable membrane 132 and/or comprises a flow control valve 138, the bladder 130 may be made from an elastic or other appropriate material that permits the bladder 130 to repeatedly expand and contract to receive and dispense nutrients N to patient P. Moreover, the bladder 130 and enteral feeding or satiety-inducing device 100 also may have other appropriate configurations.

As the bladder 130 expands as shown in FIGS. 2B and 2C, the patient's stomach S swells or expands to accept the bolus of nutrients. The swelling or expansion of the patient's stomach may induce a feeling of being "full" or satiated. However, because the bladder 130 is made from a permeable material or incorporates a flow control valve or other suitable feature for slowly dispensing the nutrients, the clinical benefits of continuous drip feeding or jejunal feeding, such as reduction of reflux or aspiration, still may be achieved with device 100. As such, the patient P may be "fed" on a more normal feeding regimen, e.g., receiving two or three bolus doses of nutrients a day that simulate two or three meals, while still receiving nutrients on a continuous basis.

While various patents have been incorporated herein by reference, to the extent there is any inconsistency between incorporated material and that of the written specification, the written specification shall control. Further, this written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. An enteral feeding device, comprising:
    a catheter tube having a distal end and a proximal end;
    a first retainer secured to the catheter tube at the proximal end of the catheter tube, the first retainer being an external retainer for deployment outside a patient's body;
    a second retainer secured to the catheter tube at the distal end of the catheter tube, the second retainer being an indwelling retainer for deployment within an interior of a stomach of a patient; and
    an expandable bladder secured to the catheter tube at the distal end of the catheter tube, the expandable bladder is configured to be positioned within the stomach of the patient for receiving and dispensing nutrients to the patient.

2. The device of claim 1, wherein the bladder is a permeable membrane.

3. The device of claim 1, further comprising a flow control valve for dispensing nutrients from the bladder.

4. The device of claim 1, wherein the bladder is constructed from an elastic material.

5. The device of claim 1, wherein the bladder expands to receive a bolus dose of nutrients.

6. The device of claim 1, wherein the bladder expands to occupy a spherical volume of the stomach.

7. The device of claim 1, wherein the nutrients are dispensed at a continuous rate.

8. The device of claim 1, wherein the first retainer is a base of a low profile enteral feeding device.

9. The device of claim 1, wherein the second retainer is an inflatable balloon.

10. The device of claim 1, wherein the bladder is constructed from an elastic material.

11. The device of claim 1, wherein the retainer is a base of a low profile enteral feeding device.

12. The device of claim 1, wherein the retainer is a first retainer, and wherein the device further comprises a second, indwelling retainer.

13. The device of claim 12, wherein the second retainer is an inflatable balloon.

14. A satiety-inducing device for continuously dispensing nutrients to a patient, the device comprising:
    an enteral feeding tube having a distal end and a proximal end, the distal end positionable within a stomach of the patient;
    a retainer secured to the feeding tube at the proximal end of the feeding tube, the retainer being an external retainer for deployment outside the patient's body; and
    an expandable bladder secured to the feeding tube near the distal end of the feeding tube such that the expandable bladder is positionable within the stomach of the patient,
    wherein the expandable bladder expands upon receipt of nutrients to occupy a volume of an interior of the stomach and contracts as nutrients are continuously dispensed to the patient.

15. The device of claim 14, wherein the bladder is a permeable membrane.

16. The device of claim 14, further comprising a flow control valve for controlling a flow rate of nutrients from the bladder.

17. An enteral feeding device, comprising:
    a catheter tube having a distal end and a proximal end;
    a first retainer secured to the catheter tube at the proximal end of the catheter tube, the first retainer being an external retainer for deployment outside a patient's body;
    a second retainer secured to the catheter tube at the distal end of the catheter tube, the second retainer being an indwelling retainer for deployment within a stomach of a patient; and
    an expandable bladder secured to the catheter tube at the distal end of the catheter tube, the expandable bladder is configured to be positioned within the stomach of the patient for receiving and dispensing nutrients to the patient,
    wherein the catheter is configured to be positioned through a stoma formed through a wall of the stomach and the patient's skin such that the catheter spans from an interior of the stomach to an exterior of the patient.

18. The device of claim 17, wherein the first retainer is a base of a percutaneous transconduit device having a proximal surface and a distal surface, and wherein the distal surface is positioned in contact with the patient's skin.

19. The device of claim 17, wherein the bladder is configured to expand the patient's stomach upon receipt of a bolus dose of nutrients in the bladder.

20. The device of claim 17, wherein the bladder comprises a flow control valve for controlling a flow rate of nutrients from the bladder.

* * * * *